(12) United States Patent
Bjerregaard et al.

(10) Patent No.: US 9,480,816 B2
(45) Date of Patent: Nov. 1, 2016

(54) INCONTINENCE TREATMENT DEVICE PACKAGE

(71) Applicant: Coloplast A/S, Humlebaek (DK)

(72) Inventors: Henrik Bork Bjerregaard, Broenshoej (DK); Marlene Corydon, Espergaerde (DK); Henrik Lindenskov Nielsen, Smoerum (DK)

(73) Assignee: Coloplast A/S, Humlebaek (DK)

( * ) Notice: Subject to any disclaimer, the term of this patent is extended or adjusted under 35 U.S.C. 154(b) by 238 days.

(21) Appl. No.: 14/179,564

(22) Filed: Feb. 13, 2014

(65) Prior Publication Data

US 2014/0158568 A1    Jun. 12, 2014

Related U.S. Application Data

(63) Continuation of application No. 13/658,832, filed on Oct. 24, 2012, now Pat. No. 8,684,984, which is a continuation of application No. 12/083,013, filed as application No. PCT/EP2005/054976 on Oct. 3, 2005, now abandoned.

(51) Int. Cl.
| | |
|---|---|
| *A61F 5/451* | (2006.01) |
| *A61F 5/453* | (2006.01) |
| *A61M 25/00* | (2006.01) |
| *A61F 6/00* | (2006.01) |

(52) U.S. Cl.
CPC ............ *A61M 25/002* (2013.01); *A61F 5/453* (2013.01); *A61F 6/005* (2013.01); *Y10T 29/49826* (2015.01)

(58) Field of Classification Search
CPC ..... A61F 5/453; A61F 6/005; A61M 25/002
See application file for complete search history.

(56) References Cited

U.S. PATENT DOCUMENTS

| | | | | | |
|---|---|---|---|---|---|
| 3,983,996 | A * | 10/1976 | Hendren, III | .......... | A61B 50/20 206/363 |
| 4,332,322 | A * | 6/1982 | Jaeschke | ............. | A61M 25/002 206/363 |
| 4,674,676 | A * | 6/1987 | Sandel | ............... | A61B 19/0287 206/366 |
| 4,781,288 | A * | 11/1988 | Wing | ..................... | A45C 11/24 132/293 |
| 4,805,820 | A * | 2/1989 | Kearney | ................. | A61F 6/005 206/37 |
| 5,050,623 | A * | 9/1991 | Yuhara | ................... | A45D 40/22 132/293 |
| 5,133,454 | A * | 7/1992 | Hammer | .............. | B65D 25/105 206/364 |
| 5,316,019 | A * | 5/1994 | Jones | ...................... | A61F 6/005 128/844 |
| 5,427,233 | A * | 6/1995 | Zinck | ...................... | A61F 6/005 206/37 |
| 5,862,908 | A * | 1/1999 | Arbin | ...................... | A61F 6/005 206/37 |
| 8,002,113 | B1 * | 8/2011 | Cummings | ........ | B65D 83/0847 206/408 |
| 2001/0035358 | A1 * | 11/2001 | Woodhouse | ............ | A61F 6/005 206/69 |
| 2004/0020814 | A1 * | 2/2004 | Mousset | ............ | A61B 19/0264 206/438 |
| 2004/0182729 | A1 * | 9/2004 | Farrar | ..................... | A61F 17/00 206/349 |
| 2009/0071851 | A1 * | 3/2009 | Maki | ................... | A61M 25/002 206/210 |
| 2010/0071703 | A1 * | 3/2010 | Felitsyn | .................... | A61F 6/00 128/844 |
| 2013/0092563 | A1 * | 4/2013 | Wedel | ...................... | B65B 7/28 206/69 |

* cited by examiner

*Primary Examiner* — Susan Su
(74) *Attorney, Agent, or Firm* — Coloplast Corp., Coloplast A/S; Nick Baumann

(57) ABSTRACT

A packaged incontinence treatment device includes a catheter enclosed in a package having a closure jaw. The package has a lower portion coupled to an upper portion by a hinge plate that forms a rear wall of the package. The hinge plate allows the upper portion to pivot away from the lower portion to open the package. The closure jaw includes a first wall that is attached to the lower portion by a hinge line and an overlap wall that is attached to the first wall by a front wall. The overlap wall is releasably secured to the upper portion of the package.

14 Claims, 4 Drawing Sheets

INCONTINENCE TREATMENT DEVICE PACKAGE

TECHNICAL FIELD

The present invention relates to a male incontinence product and a package therefor. The incontinence product comprises a penile sheath which is rolled up to form a collar portion, when the product is in the package. The incontinence product further comprises a drainage portion for connecting a cavity of the sheath to a urine-collecting bag. In literature, male incontinence products of the present type may also be referred to as external catheters, uridoms or urisheaths.

BACKGROUND OF THE INVENTION

WO 91/17728 discloses a male incontinence product of the above-mentioned type. The incontinence product comprises a penile sheath, or "body portion", which is delivered to the user in a rolled-up configuration, in which the penile sheath is rolled-up to form a proximal collar portion. During use, the sheath forms a tight fit around the user's penis. Optionally, an adhesive is provided on an inner surface of the sheath. The cavity formed by the sheath communicates with a distal drainage portion, or "drainage tube", of the incontinence product to allow urine to flow into a urine collecting bag. Compared to the penile sheath, at least a distal tubular part of the drainage portion has a relatively large wall thickness, so as to enable connection thereof to the urine collecting bag. The drainage portion may comprise a funnel-like part forming a transition between the sheath and the distal tubular part of the drainage portion. The urine collecting bag does not normally form an integral part of the incontinence product and is usually provided as a separate entity to the user. During use, the urine collecting bag may conveniently be fastened to one of the user's legs.

FIG. 1 illustrates a male incontinence product 100 of the above type, arranged in a prior art package 102. The package comprises two foils of a plastics material, which are torn apart at one of two end zones 104 when the package is to be opened. In the package, the incontinence product is stored in a ready-to-use configuration with a distal tubular end portion 106 coextending with a bellow-shaped connecting portion 108 and with the penile sheath rolled up to form a proximal collar portion 110. It will hence be understood that the drainage portion comprises the distal tubular portion 106 and the bellow-shaped connecting portion 108. The package may be generally opaque, as illustrated in FIG. 1, with a transparent window 112, through which the incontinence product 100 is visible from the outside. The dimensions of the package of FIG. 1 may vary with the specific dimensions of the product accommodated in the package. Generally, the package measures 8-10 cm by 10-15 cm and has a thickness of 3-5 cm.

The prior art package of FIG. 1 is rather space consuming, as the incontinence product, unlike a contraceptive, features the above-mentioned longitudinally extending drainage portion. Additionally, the package has a tendency to crackle when handled or even when simply accommodated in a user's pocket. For these reasons, the package of FIG. 1 is not as discrete as sometimes desirable. It is therefore an object of embodiments of the present invention to provide a combination of a male incontinence product and a package therefor which is discrete, and which occupies less space than prior art packages. It is a further object of embodiments of the present invention to provide such a combination, which is convenient in use, and which may be manufactured at reasonable costs. It is a still further object of embodiments of the present invention to provide a method for manufacturing a combination of a male incontinence product and a package therefor, which method allows for automated and cost-efficient packaging, and which results in a combination of an incontinence product and a package overcoming at least some of the disadvantages of prior art packages.

SUMMARY OF THE INVENTION

In a first aspect, the invention provides a combination of a male incontinence product and a package accommodating the incontinence product in a rolled-up configuration thereof, the incontinence product comprising:
  a penile sheath, which during use is unrolled to define a cavity for a length of the user's penis, and which, in the rolled-up configuration of the incontinence product, is rolled up to form a proximal collar portion of the incontinence product; and
  a drainage portion for connecting the cavity of the sheath to a urine-collecting device, e.g. a urine collecting bag;
  whereby at least one of the penile sheath and the drainage portion is sufficiently flexible to allow collapsing of the incontinence product when in its rolled-up configuration;
  the combination further comprising at least one retention element, which retains the rolled-up incontinence product in a collapsed state.

It will be appreciated that the present combination allows for compact storage of the incontinence product, as the retention element ensures that the product is retained in its collapsed state in the package, typically when the package is closed. In one embodiment, the incontinence product may be collapsed by simple compression or flattening of the collar portion to reduce the transverse extent of the incontinence product, i.e. pressing the collar sides against each other. In other embodiments, the drainage portion may alternatively or additionally be bent away from its initial position, i.e. such that a centre axis of the drainage portion, or a centre axis of a part of the drainage portion, does not co-extended with a centre axis of the rolled-up sheath. Thereby the longitudinal extent of the incontinence product is reduced. For example, a funnel-like proximal part of the drainage portion may be bent or folded in the collapsed state, or the drainage portion may be bent at a transition between a distal tubular part of the drainage portion and the funnel-like proximal part. The funnel-like part may e.g. be bellow-shaped to achieve mechanical stability and improved bending capabilities. In this case the collapsed state may be achieved by folding-up of the bellow-shaped interconnecting portion, whereby the longitudinal extent of the incontinence product is reduced without bending the distal tubular part of the drainage portion away from its initial position. It is also contemplated that the distal tubular part itself may be bellow-shaped or capable of being rolled up to allow an even more compact collapsed configuration.

The penile sheath and the drainage portion may be made from a latex material as elaborated in WO 91/17728. Typically the material of the sheath and the drainage portion is chosen from the groups of cross-linked elastomers or thermoplastic elastomers. Cross-linked elastomers can for example be latex and silicones, and thermoplastic elastomers can for example be SEBS (styrene-ethylene-butylene-styrene). Thus, in other embodiments, the sheath and drainage portion are made from a silicone material or alternatively a SEBS material, which has the advantage over latex that essentially no permanent deformation of the material occurs, even if the incontinence product has been stored in the collapsed state for a long period of time, such as e.g. one year.

In embodiments of the present invention, the retention element may be integral with a wall of the package, such that when the package is opened and/or when the incontinence product is removed from the package, the product undergoes a transformation from its collapsed state to its ready-to-use, non-collapsed state. For example, the retention element may be constituted by a portion of the package. Alternatively, the retention element may be tied around the incontinence product in the collapsed configuration and the retention element may for example comprise a flexible element, rubber band or a strip. In the latter embodiment, the package may, in addition to the strip, comprise a bag or pouch made from e.g. a plastics foil to prevent contamination of the incontinence product. The strip may be connected to the bag or pouch, or it may be a separate entity connected only to the incontinence product. The retention element may furthermore be provided with two grips, for example formed as a part of the strip. When the grips are pulled apart the strip is torn or otherwise opened allowing the incontinence product to enter its non-collapsed state.

The package may comprise an upper and a lower substantially rigid package portion manufactured e.g. by injection moulding of a plastics material. In the present context, "substantially rigid" is intended to mean that the package portions feature sufficient rigidity to prevent the incontinence product from unfolding when it is accommodated in the package. Preferably the shape and dimensions of each package portion are substantially non-transformable by hand. In one embodiment, the upper package portion may form a screw cap for the lower package portion. Alternatively, the upper and lower package portions may be secured by a frictional interconnection, by a snap interconnection or by a strip. In yet another alternative, only the lower package portion is rigid, whereas the upper package portion comprises a foil to be peeled off the lower package portion. A still further alternative is to provide a sliding interconnection, i.e. to provide the upper package portion in the form of a sliding lid. Finally, as described in further detail below, the upper and lower package portions may be hinged at a hinge element provided at an edge portion of the package. Conveniently, a protrusion for engaging the collar portion as described in more detail below may be integral with the hinge element.

In order to at least partially retain the incontinence product relative to the package, a protrusion may be provided in the package, which engages the collar portion. The protrusion may e.g. extend from the hinge element or from a side wall of one of the package portions. As an alternative or further measure, there may be provided one or more protrusions extending centrally with respect to the collar portion and/or the drainage portion, either at an inside thereof or at an outer surface thereof.

Handling of the present combination may be facilitated if the incontinence product biases one of the package portions away from the other. In such embodiments, the package may comprise a closing element retaining the upper and lower package portions in a closed configuration. Thus, when the closing element is released to open the package, the incontinence product assists in opening the package. Preferably, the package allows the incontinence product to unfold to its non-collapsed, ready-to-use configuration upon opening of the package without any need for handling of the incontinence product. Thus, user-handling of the incontinence product is limited to removal of the product from the package and subsequent application. The closure element retaining the upper and lower package portions in the closed package configuration may comprise a jaw element, which is hinged to one of the lower and upper package portions, and which is arranged to releasably engage the other one of the package portions. Such releasable engagement may e.g. be achieved by a notch-protrusion interconnection. The required releasability may conveniently be achieved by the elasticity of the material(s) from which the package portion concerned and the jaw element is/are made. In order to provide a secure grip for the user, the jaw element may extend the entire width or length of the package, and an end portion of the jaw may form a gripping edge. It has been found that the package may be held securely in its closed configuration if a first portion of the jaw element forms a continuation of that one of the package portions, to which it is hinged. For example, if the jaw element is hinged to the lower package portion, the first portion of the jaw element may form an extension of, or part of, a lower surface of the package, rather than simply being hinged to a far end edge of the lower surface. Likewise, a second portion of the jaw element may overlap at least a portion of that other package portion, to which the first jaw portion is not hinged. For example, the second portion of the jaw element may overlap the upper package portion when the package is closed. Conveniently, the jaw element is provided at an edge of the package, which is opposite to that edge, at which the hinge element interconnects the upper and lower package portions.

It will be appreciated that storage of the incontinence product in the collapsed state in the package confers the possibility of a compact package design. In embodiments of the present invention, the package is relatively flat when closed, i.e. such that a height of the package is at most ⅓ of a width or diameter of the package, such as at most ¼ or ⅕ of the width or diameter. The width or diameter of the package is typically in the range of 30-80 mm, such as 30-70 mm, such as 30-60 mm, such as 35-60 mm. In the present context, the term "width or diameter" is to be understood as the largest cross-sectional dimension of the package in a plane projection. The height of the package is typically in the range of 5-20 mm, such as 5-15 mm, such as 7-13 mm, such as 8-12 mm. The height need not be constant throughout the entire width of the package. If, for example, the drainage portion of the incontinence product is bent or folded away from is initial position in the collapsed state, the drainage portion will normally extend beyond the periphery of the collar portion. If a distal end of the drainage portion may be compressed to a height smaller than the height of remaining portions of the collapsed incontinence product, then that portion of the package, which accommodates the distal end of the drainage portion, may likewise have a smaller height than remaining portions of the package. It is preferable that a lower surface of the package is essentially planar to achieve a stable support on a planar surface, e.g. a desk.

At least one of the upper and lower package portions may have a thickened portion. The thickened portion may e.g. be provided for purposes of reinforcement. However, the thickened portion may also be provided in order to optimize manufacture of the package, e.g. by injection moulding. If, for example, the package is manufactured by injection moulding as one single element, transport of liquefied plastics material from an inlet of a mould to remote zones of the mould is aided by the presence of a groove or trail in the mould, which results in the aforementioned thickened portion in the package. By optimising the manufacture as described a lightweight package can furthermore be provided as the remaining material can be formed relatively thin compared to the thickened portion.

As previously discussed, the package may comprise upper and lower package portions, which are mutually hinged by a hinge element. In one embodiment, the hinge element may be hinged to the lower package portion at a bottom surface of the lower package portion, and likewise it may be hinged to the upper package portion at a top surface of the upper package portion. Thus, in a closed configuration of the package, the hinge element forms part of an end wall of the package, whereby a height of the hinge element is essentially equal to the height of the package. At least one of the upper and lower package portions, and preferably both package portions, may define an upright edge wall to keep the package portions at a controlled mutual distance when the package is closed and to prevent contaminants from entering the package. The edge walls and the hinge element may be arranged such that at least one of the edge walls and the hinge element comprises a protrusion allowing the edge wall and the hinge element to enter (or "click") into mutual engagement. In one embodiment, each of the free ends of the hinge element comprises such a protrusion, which may releasably click the hinge element into engagement with the edge wall of the lower package portion. The edge walls of the upper and lower package portions may be shaped to constitute mutual guides to ensure proper alignment of the package portions when the package is being closed and to contribute to mechanical stability of the package.

In a second aspect the present invention provides method for manufacturing a combination of a male incontinence product and a package therefor, wherein the male incontinence product comprises:

a penile sheath, which is rolled up to form a proximal collar portion of the incontinence product, and a drainage portion for connecting a cavity of the sheath to a urine-collecting bag, whereby at least one of the penile sheath and the drainage portion is sufficiently flexible to allow collapsing of the incontinence product when in its rolled-up configuration; the method comprising the steps of:
providing the package in an open state thereof;
placing the incontinence product in the package;
collapsing the incontinence product; and
closing the package in such a way that the incontinence product is retained in its collapsed state in the closed package.

Accordingly, a combination of an incontinence product and a package featuring the benefits and advantages described above in connection with the first aspect of the invention may be manufactured by embodiments of the present method. It will be appreciated that the method may be performed in an automated manner at low cost. It should be noticed that the steps not necessarily occur in the order mentioned, for example in one presently preferred embodiment, the steps of collapsing and closing occur essentially simultaneously.

One embodiment of the present method is for the manufacture of a combination, of which the package comprises an upper and a lower substantially rigid package portion, and a hinge element which is hinged to the lower package portion at a bottom surface of the lower package portion, and which is hinged to the upper package portion to a top surface of the upper package portion. Thus, the package may initially be provided in a configuration, in which the hinge element essentially coextends with the aforementioned bottom and top surfaces. In this configuration, the incontinence product may be placed at the bottom surface of the lower package portion, and subsequently the hinge element may be entered into engagement with an upright edge wall defined by one of the upper and lower package portions. Such engagement may be achieved by protrusions at the hinge element as discussed in above in connection with the first aspect of the invention. This design of the package and the assembling process made possible thereby confer further advantages with respect to achieving a cost-efficient, automated method of assembling.

The step of providing the package may comprise casting at least a portion of the package by injection moulding. Preferably, the entire package is injection moulded in one single piece.

The package can be made of many different types of materials. Typically plastics, such as polypropylene, are used. Alternatively, as the package is usually disposed after the incontinence product has been used, the product can advantageously be made of a biodegradable material, such a paper mixed with a soluble starch or a biodegradable plastic.

The method of the second aspect of the invention may further comprise appropriate steps for arriving at those features and characteristics of the combination of the first aspect of the invention, which are described herein.

BRIEF DESCRIPTION OF THE DRAWINGS

Embodiments of the present combination of a male incontinence product and package therefor as well as of the present method will hereinafter be described with reference to the drawings, in which.

DETAILED DESCRIPTION OF THE DRAWINGS

Figure 1:
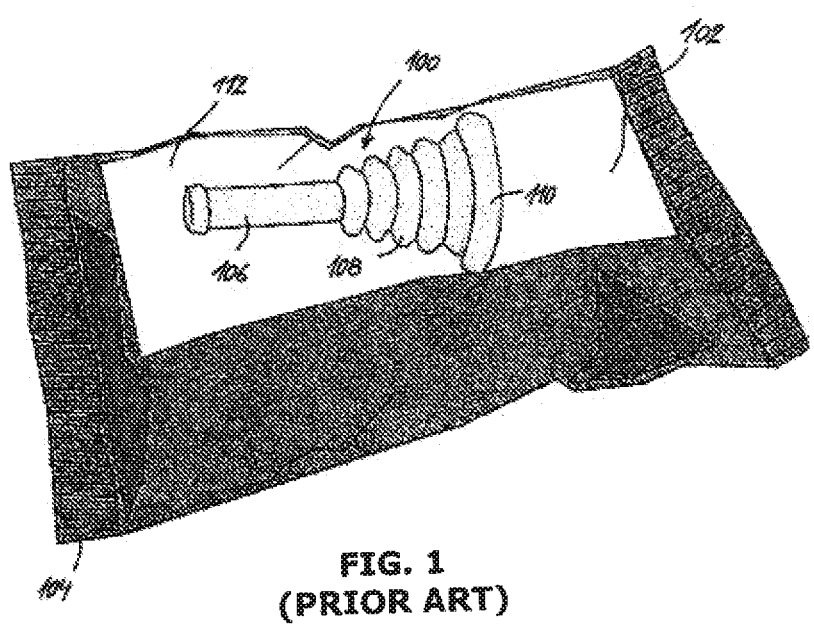
FIG. 1 illustrates a prior art combination of a male incontinence product and package.

The prior art package of FIG. 1 is described in connection with the background of the invention above.

Figure 2:
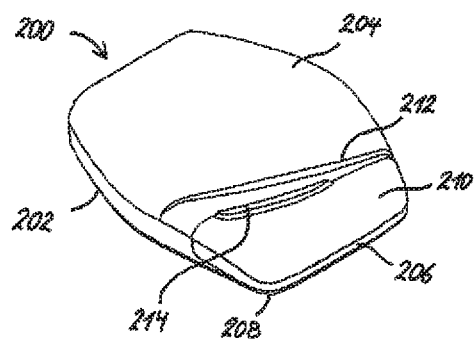
FIGS. 2-5 illustrate a first embodiment of the combination of the present invention.
Figure 3:
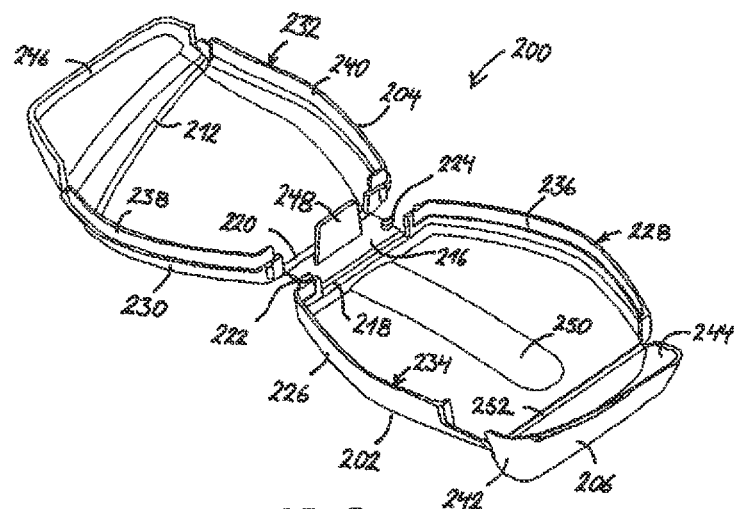
Figures 4, 5:
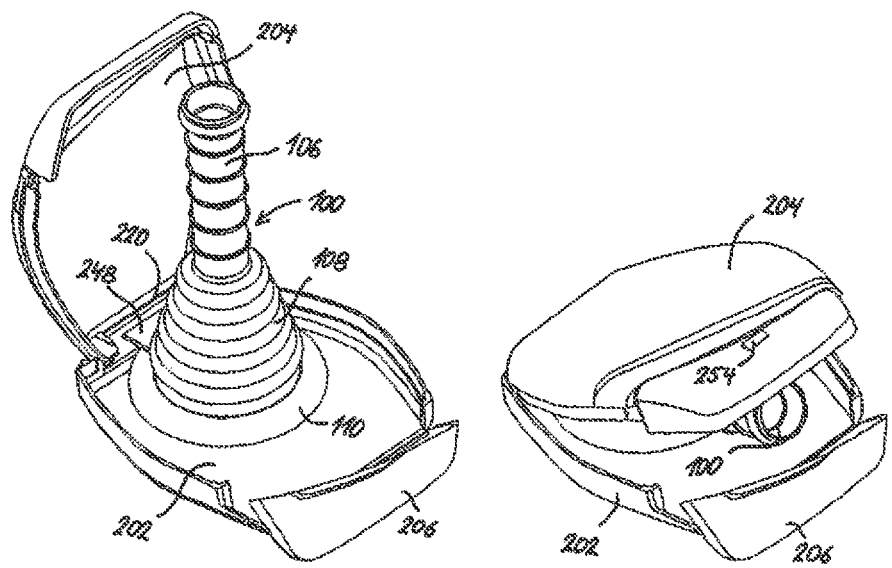

In the embodiment of FIGS. 2-5, the package 200 is shown in its closed configuration in FIG. 2, accommodating a male incontinence product. The package includes a lower package portion 202 and an upper package portion 204, which are permanently interconnected by means of a hinge as illustrated in FIGS. 3 and 4. A closure element is provided in the form of a jaw element 206 formed integrally with the lower package portion 202 via a hinge connection allowing the jaw element to pivot away from its position of FIG. 2, in which it engages the upper package portion 204 to keep the package closed, to the position of FIGS. 3-5, in which it does not engage the upper package portion. The jaw element 206 has a first, lower portion 208, which in the closed configuration of FIG. 2 coextends with and forms an extension of a lower surface of the lower package portion 202. A second portion 210 of the jaw element 206 overlaps and engages and end section of the upper package portion 204. To facilitate the user's handling of the jaw element 206 to open the package, a gripping section 214 is formed at the jaw element, and a step 212 is formed at the upper package portion 204 to provide space for one or more of the user's finger tips. The user may conveniently open the package by placing his thumb parallel with the gripping section 214 and by then engaging the gripping section with his thumb.

Once the package has been manufactured, preferably by injection moulding thereof, the package is initially provided in the configuration of FIG. 3, in which a hinge element 216 interconnecting the upper and lower package portions essentially coextends with a bottom surface of the lower package portion 202 and with a top surface of the upper package portion 204, which in the configuration of FIG. 3 faces downwardly. In this configuration, an incontinence product 100 (cf. FIG. 4) is placed in the package with its collar portion 110 supported by the lower package portion 202. Subsequently, the upper package portion 204 is pivoted towards the lower package portion 202 around the hinge element 216, the hinge element being connected to the upper and lower package portions along hinge lines 218 and 220 of reduced wall thickness. During the transition from the configuration of FIG. 3 to the configuration of FIG. 4, protrusions 222 and 224 of the hinge element 216 click into engagement with upright edge walls 226 and 228 of the lower package portion, whereby the hinge element is no longer free to pivot around hinge line 218. Only the upper package portion may now pivot around hinge line 220.

FIG. 3 further illustrates upright edge walls 230 and 232 of the upper package portion. The edge walls 230 and 232 are arranged such that they, upon closing of the package, engage the edge walls 226 and 228 of the lower package portion. The edge walls 226 and 228 form guides 234 and 236 for mating guides or rails 238 and 240 of the upper edge walls 230 and 232. The jaw element 206 forms side walls 242 and 244 which in the closed configuration of FIG. 2 coextend with the upright edge walls 226, 228, 230 and 232. Additionally, to reduce the risk of contamination of the incontinence product in the package, a free end portion of the upper package portion 204 is provided with a wall element 246.

The hinge element 216 includes a further protrusion 248, which in the configuration of FIG. 4 faces inwardly, i.e. towards the incontinence product in the package. The protrusion 248 overlaps and engages the collar portion 110 of the incontinence product, so as to retain it relative to the lower package portion. Preferably, the upright distance between the protrusion 248 in the configuration of FIG. 4 is slightly smaller than the height of the collar portion 110, e.g. 0.5 mm smaller to provide a firm, but yet easily releasable grip on the collar portion.

FIG. 3 further illustrates a thickened portion 250 in a bottom surface of the lower package portion 202, formed by a groove in a mould of an injection moulding machine, in which the package is preferably formed in one single piece. The groove in the mould and thus the thickened portion 250 extend from the hinge element 216, at which an injection inlet may be provided, so as to aid liquefied plastics material to distribute evenly in the lower package portion. FIG. 3 additionally shows a hinge line 252, at which the jaw element 206 is pivotally connected to the lower package portion 202.

Following placement of the incontinence product in the lower package portion and transition of the upper package portion to the configuration of FIG. 4, the upper package portion is moved further towards the lower package portion by pivoting around hinge line 220. Thereby an inwardly facing portion of the wall element 246 (cf. FIG. 3) engages a tip of a distal tubular part 106 of the drainage portion of the incontinence product. As the upper package portion is pivoted further towards the lower package portion, the upper package portion causes the drainage portion 206 to kink at a transition between the distal tubular part 106 of the drainage portion and a bellow-shaped proximal part 108 of the drainage section. At the same time, a distal portion of the bellow-shaped part 108 bends with the distal tubular part 106, whereas the remainder of the bellow-shaped part 108 is being compressed as the upper package portion moves closer to the lower package portion. FIG. 5 shows an intermediate configuration of the package accommodating the incontinence product immediately prior to the totally closed configuration of FIG. 2. FIG. 5 shows that a protrusion 254 is provided at the upper package portion 204. In the closed configuration of FIG. 2, the protrusion 254 engages a mating notch in a downwardly facing surface of the second portion 210 of the jaw element 206 (cf. FIG. 2). This notch-protrusion connection provides a secure, releasable and re-closable fit between the jaw element 206 and the upper package portion to keep the package closed. The fit should be strong enough to counteract that force, which the collapsed incontinence product in the package provides, as it is biased towards its initial non-collapsed state of FIG. 4. It has been found that stability of the jaw closure mechanism is improved by letting the first portion 208 of the jaw element form an extension of the lower surface of the lower package portion. Likewise, the overlap of the upper portion 210 of the jaw element improves stability of the package.

When the package is to be opened, the jaw element 206 is released from the upper package portion, and the biasing force of the incontinence product causes the upper package portion to pivot around hinge line 220 (cf. FIG. 4) to the position of FIG. 4. The user can then place the package on a surface, such as on a sink, where it will rest with minimal risk of contamination while he cleans himself. The user may then remove the incontinence product from the package and apply it.

Figure 6:
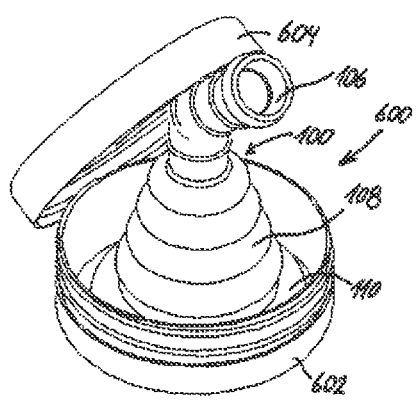
FIGS. 6-10 illustrate further embodiments of the combination of the present invention.
Figure 7:
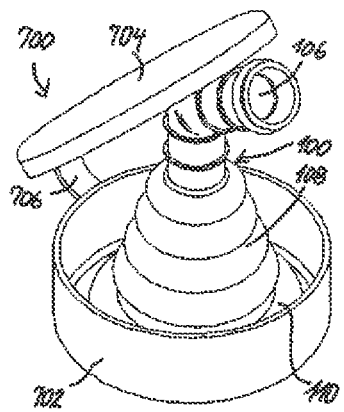
Figure 8:
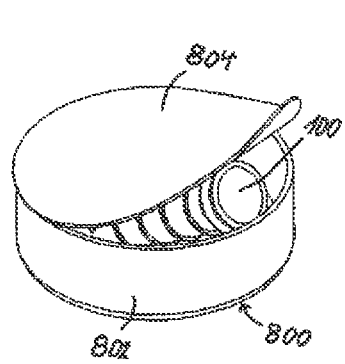

In the embodiment of FIG. 6, the package 600 comprises a lower package portion 602 and an upper package portion in the form of a screw cap 604. FIG. 7 illustrates a further embodiment, in which the package 700 includes a lower package portion 702 and a lid 704 with a downwardly facing rim portion intended to frictionally engage a cylindrical wall of the lower package portion 702. A strip 706 interconnecting the lid and the lower package portion is provided to prevent the lid from being lost. FIG. 8 illustrates a yet further embodiment of a package 800, in which the incontinence product is accommodated in a lower package portion 802 closed by a peelable foil 804. In the package 900 of FIG. 9, the upper and lower package portions 902 and 904 have a rectangular shape allowing the upper package portion to slide relative to the lower package portion as indicated by arrow 908. A depression 906 is provided in the upper package portion for facilitating opening of the package. In the embodiment of FIG. 10, the package 1000 comprises a lower package portion 1002 accommodating at least a portion of the incontinence product. A strip 1004 is tied around the lower package portion 1002 and the incontinence product to retain the incontinence product in its collapsed state. The package 1000 may further include a pouch or bag (not shown) to protect the incontinence product from contamination. In an alternative embodiment (not shown) resembling that of FIG. 10 the lower package portion 1002 is not provided and only the strip 1004 retain the incontinence product in its collapsed state.

Figure 9:
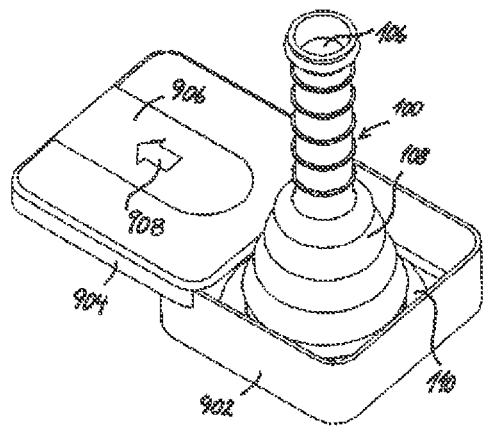
Figure 10:
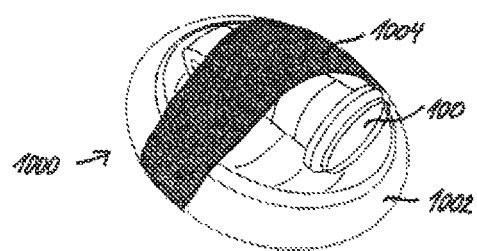

In the above embodiments of FIGS. 2-9, the retention element, which retains the rolled-up incontinence product in its collapsed state when the package is closed, generally comprises the respective upper package portions and their interconnections to the respective lower package portions. Thus, in the embodiment of FIGS. 2-5, the retention element comprises the upper package portion 204 and the jaw element 206. In the embodiment of FIG. 6, the retention element comprises the screw cap 604 with it inner threads as well as the outer threads provided at the lower package portion 602. In the embodiment of FIG. 7, the retention element includes the lid 704 with its peripheral rim, which frictionally engages the lower package portion 702. In FIG. 8, the retention element includes the peelable lid 804 and its adhering connection to the lower package portion 802. In the embodiment of FIG. 9, the retention element includes the slidable lid 904 and its engagement with the lower package portion 902. Finally, in FIG. 10, the retention element comprises the strip 1004 and its interconnection with the lower package portion 1002.

In all of the above embodiments, a seal may be provided which is irreversibly broken when the package is opened for the first time. Accordingly, the user may verify that the package has not been opened previously.

The dimensions of the packages of FIGS. 2-10 may vary with the dimensions of the specific incontinence products accommodated thereby. Generally, the dimensions of the packages are about 4-6 cm by 5-7 cm, and the height of the packages when closed is about 8-12 mm.

Using the packaging disclosed it is furthermore possible to save considerable space during transport of the incontinence product. For example a box packed with thirty pieces of incontinence products packed in the packaging illustrated in FIGS. 2-5 have a volume of 1500 cm³. Compared to a box packed with thirty pieces of incontinence products packed in the prior art package as shown in FIG. 1, which has a volume of 6800 cm³, a box packed with the packages illustrated in FIGS. 2-5 takes up less than one fourth the space. Such a reduction in space not only provides for cheaper transport and storage costs, but also creates more freedom for the user as he can carry a larger number of products or alternatively store a few products more discreetly than before.

What is claimed is:

1. A packaged incontinence treatment device comprising:
    an external catheter including a discharge tube attached to a sheath, with a length of the sheath rolled-up toward the discharge tube; and
    a package enclosing the catheter, the package having a lower portion coupled to an upper portion by a hinge plate, with a height of the package defined as a distance between the lower portion and the upper portion when the package is in a closed configuration;
        wherein the hinge plate is integrated with the lower portion and with the upper portion to provide an end wall of the package, and the hinge plate is adapted to allow the upper portion to pivot away from the lower portion to provide an opened package configuration and to allow the upper portion to pivot toward the lower portion to provide the closed package configuration.

2. The packaged incontinence treatment device of claim 1, wherein a height of the hinge plate is equal to the height of the package.

3. The packaged incontinence treatment device of claim 1, wherein the package comprises a closure jaw located opposite of the hinge plate, the closure jaw adapted to secure the upper portion in a substantially parallel relationship to the lower portion when the package is in the closed package configuration.

4. The packaged incontinence treatment device of claim 3, wherein the lower portion of the package has lower opposed lateral edge walls that extend from the hinge plate to the closure jaw and the upper portion of the package has upper opposed lateral edge walls that extend from the hinge plate to the closure jaw.

5. The packaged incontinence treatment device of claim 3, wherein an edge of the closure jaw provides a gripping element and an exterior surface of the upper portion forms a relief step, the gripping element and the relief step combining to provide a space between the closure jaw and the upper portion when the package is in the closed package configuration.

6. The packaged incontinence treatment device of claim 3, wherein the package provides a releasable and reclosable securement mechanism including a notch formed on the closure jaw that is adapted to mate with a closing protrusion provided on the exterior surface of the upper portion.

7. The packaged incontinence treatment device of claim 3, wherein the closure jaw is attached to the lower portion of the package by a hinge line.

8. The packaged incontinence treatment device of claim 3, wherein the closure jaw is movable relative to the lower portion of the package.

9. The packaged incontinence treatment device of claim 1, wherein the package comprises a retainer protrusion extending from an interior surface of the lower portion of the package, the retainer protrusion configured to engage with and retain the external catheter in the lower portion of the package.

10. The packaged incontinence treatment device of claim 1, wherein the hinge plate includes a click protrusion that is adapted to engage with an edge wall of the lower portion.

11. A packaged incontinence treatment device comprising:
    a catheter enclosed in a package, the package comprising:
        a lower portion coupled to an upper portion by a hinge plate that forms a rear wall of the package, the hinge plate is adapted to allow the upper portion to pivot away from the lower portion to open the package;
        a closure jaw that is attached to the lower portion of the package and releasably secured to the upper portion of the package; and
        a retainer protrusion extending from an interior surface of the hinge plate, the retainer protrusion is configured to retain the catheter in the lower portion of the package.

12. The packaged incontinence treatment device of claim 11, wherein the closure jaw includes a first wall that is attached to the lower portion by a hinge line and an overlap wall that is attached to the first wall by a front wall, and the overlap wall is releasably secured to the upper portion of the package.

13. The packaged incontinence treatment device of claim 11, wherein a front wall is provided and is located opposite of the hinge plate.

14. The packaged incontinence treatment device of claim 11, wherein an exterior surface of the upper portion forms a relief step that provides a relief space between an overlap wall of the package and the upper portion.

* * * * *